United States Patent [19]

Grauer et al.

[11] Patent Number: 5,250,297
[45] Date of Patent: Oct. 5, 1993

[54] TUMOR-ASSOCIATED ANTIGEN, ANTIBODIES, COMPOSITIONS AND USES THEREFOR

[75] Inventors: Lana S. Grauer, Del Mar; Julia P. Leung; Barry S. Wilson, both of San Diego, all of Calif.

[73] Assignee: Hybritech Incorporated, San Diego, Calif.

[21] Appl. No.: 939,384

[22] Filed: Aug. 31, 1992

Related U.S. Application Data

[63] Continuation of Ser. No. 424,845, Oct. 20, 1989, abandoned.

[51] Int. Cl.$^5$ ............................ A61K 39/00; C07K 15/00
[52] U.S. Cl. ............................ 424/88; 530/350; 530/395; 530/388.8; 530/403
[58] Field of Search ............ 424/88; 530/350, 395, 530/403, 388.8, 388.85

[56] References Cited

U.S. PATENT DOCUMENTS 5,081,032  1/1992  Yoshida et al. ............... 435/240.27
5,171,665 12/1992  Hellstrom et al. ............... 435/7.23

FOREIGN PATENT DOCUMENTS 155172  9/1985  European Pat. Off. .
218257  4/1987  European Pat. Off. .

OTHER PUBLICATIONS

Shitara, K., Hanai, N., and Yoshida, H. Distribution of lung adenocarcinoma-associated antigens in human tissues and sera defined by monoclonal antibodies KM-52 and KM-93, Cancer Res., 47:1267-1272, 1987.
Manaka, K., Nonaka, N., Yamada, T., and Hirai, H. Monoclonal antibodies against large-cell carcinoma of the lung, Dokkyo J. Med. Sci., 12: 31-41, 1985.
Morris, J. F., Krishnamurthy S., Antonovic, R., Galey, W. T., Ahmad, A., Duncan, C., and Krishnamurthy, G. Diagnosis of Lung Cancer using indium-111 murine monoclonal antibodies. American Reviews of Respiratory Diseases. 137: 290, No. sup2, 1988.
Braatz et al. (1983) Cancer Res 42, 849-855.
Bhattacharya et al. (1985) Hybridoma 4, 153-162.
Strnad et al (1989) Cancer Res. 49, 314-317.
Motte et al (1989) Cancer Res. 49, 1349-1356.
Ho et al. (1987) Cancer Res. 47, 241-250.
Dazord et al. (1987) Cancer Immunol. Immunother 24, 263-268.
Sobol et al. (1986) Cancer Res. 46, 4746-4750.
Suehiro et al. (1989) Am. J. Clin. Pathol. 92, 150-158; Abstract.

*Primary Examiner*—Robert A. Wax
*Assistant Examiner*—R. Keith Baker
*Attorney, Agent, or Firm*—June M. Bostich; Paul C. Steinhardt; Theresa A. Brown

[57] ABSTRACT

A novel tumor-associated antigen expressed by lung adenocarcinoma is disclosed. The antigen, characterized by monoclonal antibody LA20207, has a molecular weight in the range of about 50,000 to about 80,000 daltons and an isoelectric point in the range of about 4.9 to about 6.5. Antibodies directed against the antigen, methods for their production and diagnostic and therapeutic uses therefor are also provided.

3 Claims, 1 Drawing Sheet

TUMOR-ASSOCIATED ANTIGEN, ANTIBODIES, COMPOSITIONS AND USES THEREFOR

This is a continuation of co-pending application Ser. No. 07/424,845 filed on Oct. 20, 1989, now abandoned.

FIELD OF THE INVENTION

The present invention relates to the characterization of antigens, particularly tumor-associated antigens. In another aspect, it relates to antibodies having specific reactivity with such antigens and antigenic determinants thereof. In yet another aspect, it relates to methods for producing such antibodies as well as diagnostic and therapeutic uses therefor.

BACKGROUND OF THE INVENTION

The potential role of monoclonal antibodies in the diagnosis and treatment of cancer has been the focus of much recent investigation and speculation. Of particular interest are their use in immunoassays to detect and monitor the course of the disease, for example, during therapy. Also of particular interest are the potential applications of monocolonal antibodies for tumor imaging and therapy due to their capacity to bind tumor-associated antigens in vivo.

Developments in monoclonal antibody technology have also made it possible to investigate the antigenic complexity of human tumors. In particular, the specific immunoreactivity of monoclonal antibodies permits the identification and differentiation of distinct antigens expressed by human tumors. The characterization of such distinct tumor-associated antigens, therefore, provides a means to promote the production and use of monoclonal antibodies for cancer diagnosis and therapy.

Certain antigens are expressed by both human tumor cells and normal cells. These antigens are accordingly referred to not as "tumor specific" but as "tumor-associated" antigens. The diagnostic and therapeutic value of such tumor-associated antigens generally results from the excess quantity of antigen expressed by tumor cells relative to normal cells and the in vivo selectivity of antibodies for antigens expressed by tumor cells over normal cells. The ability of antibodies administered in vivo to localize with specificity at tumor sites is believed to result from: (1) the increased expression of antigen by tumor cells due to the altered and rapid metabolism of malignant growth; and, (2) the increased density of tumor cells and abnormal architecture of tumor sites relative to normal cells in surrounding tissue.

To date, only a limited number of tumor-associated antigens are well characterized. For example, antibodies that react with antigens of various lung carcinomas are described in Varki et. al., "Antigens Associated with a Human Lung Adenocarcinoma Defined by Monoclonal Antibodies," *Cancer Research* 44:681-687 (1984). According to Varki et. al., monoclonal antibodies KSl/4 and KSl/17 recognize not only three types of lung carcinomas (adenocarcinoma, epidermoid carcinoma and small-cell carcinoma) but also react with colon, breast and stomach carcinomas, while KSl/9 reacts with melanoma and adenocarcinomas of the lung, stomach, and colon. The antigens recognized by KSl/4 and KSl/9 are reported to be firmly attached in the plasma membrane. The monoclonal antibodies described in Brenner et. al., "Monoclonal Antibodies to Human Lung Tumor Antigens Demonstrated by Immunofluorescence and Immunoprecipitation," *Cancer Research* 42:3187-3192 (1982) recognize antigens located on the membranes of squamous cell carcinoma of the lung. Another human lung tumor-associated antigen from small-cell carcinoma is described in Braatz et. al., "Characterization of a Human Lung Tumor-Associated Antigen and Development of a Radioimmunoassay," *Cancer Research* 42:849-855 (1982).

Moreover, certain tumor-associated antigens useful as diagnostic or prognostic markers may not be present in all patients or during all stages and manifestations of the disease. Diagnostic discrimination and therapeutic efficacy are, therefore, enhanced by the identification and characterization of more than one tumor-associated antigen expressed by the same tumor tissue. For purposes of cancer diagnosis and therapy, it is desirable to rely on a set or panel of distinct antigens associated with specific types of human tumors. Accordingly, there exists a need for further identification and characterization of unique tumor-associated antigens.

SUMMARY OF THE INVENTION

The present invention is predicated upon the discovery and characterization of a novel antigen present in human tissue. Accordingly, the invention is directed to a substantially pure tumor-associated antigen having a molecular weight in the range of about 50,000 daltons (50 Kd) to about 80,000 daltons (80 Kd), with an isoelectric point in the range of about 4.9 to about 6.5, and a substantially pure protein epitope associated with such antigen.

In accordance with the present invention, antibodies having specificity for the antigen defined herein and methods for the production of such antibodies are also provided. Additionally, the invention is directed to the use of such antibodies for the in vitro detection and diagnosis of cancer by immunohistochemical and immunoassay methods and for the in vivo diagnosis and treatment of lung cancer in humans. The invention is also directed to pharmaceutical compositions comprising a pharmaceutically acceptable carrier and antibodies of the present invention.

DETAILED DESCRIPTION OF PREFERRED EMBODIMENTS

Figure 1:
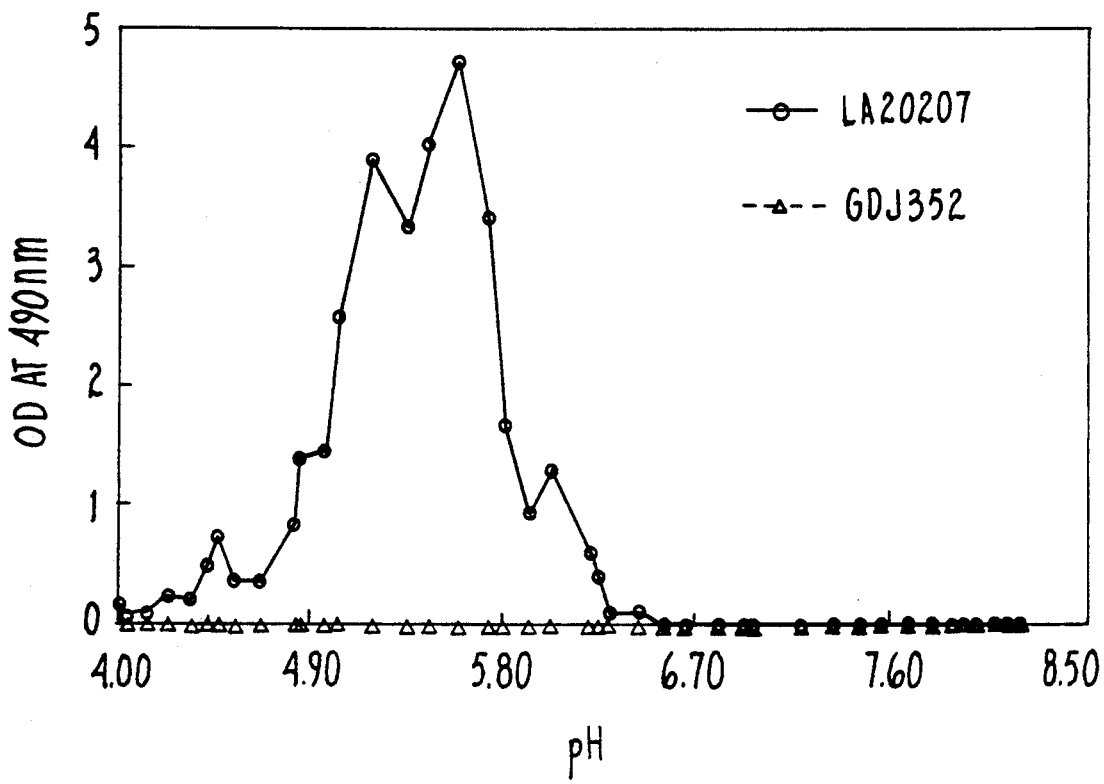
FIG. 1 depicts the isoelectric focusing pattern of the antigen recognized by monoclonal antibody LA20207.
Figure 2:
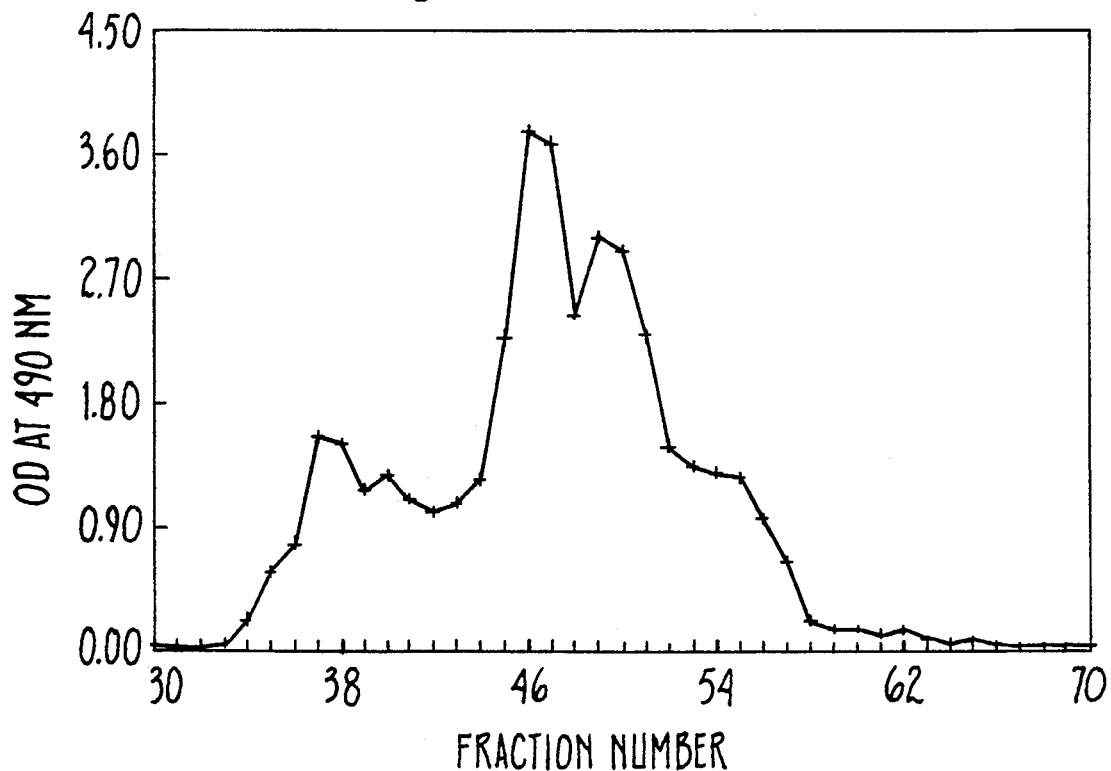
FIG. 2 shows the reactivity of LA20207 with the collected fractions of the antigen obtained by gel filtration high pressure liquid chromatography.

As indicated above, the present invention provides a substantially pure novel tumor-associated antigen having a molecular weight in the range of about 50 Kd to about 80 Kd and an isoelectric point in the range of about 4.9 to 6.5.

In accordance with the invention, monoclonal antibody LA20207, generated by hybridoma cell line ATCC #HB 10224, is utilized for the characterization of this previously undescribed antigen.

The physiochemical and immunological properties of the antigen of the present invention, and particularly its reactivity with monoclonal antibody LA20207, permit its characterization and differentiation from other antigens present in human tissue, including human tumor tissue. As used herein, cell lines refer to reproducible cells that may be grown in vitro, e.g., in tissue culture, or as xenografts on suitable animal hosts such as nude mice. The unlimited availability of cells from established cell lines distinguish them from the limited availability of cells from tissues, normal and cancerous. The term "tissue specimen" is used interchangeably with the term "tissue", which is a solid sample or other aggregation of cells performing a similar function obtained from surgery, biopsy, autopsy or otherwise extracted directly from an animal or human.

Accordingly, the identifying characteristics and properties of the antigen provided by the present invention are as follows:

(a) The antigen is present in human lung adenocarcinoma tissue. The antigen does not appear to be expressed on a wide variety of cell lines including lung adenocarcinoma cell lines. Reactivity of LA20207 with cytosol obtained from human lung adenocarcinoma and normal lung and kidney tissue has been shown by conventional ELISA techniques. In contrast, antibody LA20207 exhibits no reactivity with other normal or tumor tissues tested, including breast carcinoma, colon carcinoma, prostate carcinoma and melanoma.

(b) Standard immunohistochemical procedures demonstrate the presence of the antigen in lung adenocarcinoma as well as in normal kidney and lung tissues as shown by strong staining with monoclonal antibody LA20207. By comparison, breast carcinoma, colon carcinoma, prostate carcinoma, renal carcinoma, melanoma and other carcinomas tested showed no reactivity with LA20207.

(c) HPLC analysis indicates that the native antigen has a molecular weight in the range of about 50 Kd to about 80 Kd and a possible breakdown product having a molecular weight in the range of about 20-30 Kd.

(d) Isoelectric focusing of the antigen in solution resulted in an isoelectric point in the range of about 4.9 and about 6.5, with a peak at about 5.6.

(e) Destructive treatment studies suggest that monoclonal antibody LA20207 has specific reactivity for a conformational- dependent protein epitope of the antigen characterized herein.

Summarizing the foregoing, one aspect of the present invention is the substantially pure tumor-associated antigen characterized as having a molecular weight within the range of about 50 Kd to about 80 Kd and having an isoelectric point within the range of about 4.9 to about 6.5, with a peak at about 5.6. In addition, the tumor-associated antigen of the present invention is expressed by human lung adenocarcinoma as well as normal lung and kidney tissues.

Of particular importance in distinguishing the antigen of the present invention from other antigens, including other tumor-associated antigens, is the specificity of monoclonal antibody LA20207 for the antigen characterized herein. In describing the present invention, the term "specificity" is used interchangeably with the terms "specific reactivity" and "immunoreactivity". The specificity of LA20207 for the antigen defined by the invention provides a means for the isolation and purification of the antigen from other material and the characterization of antigenic determinants. As used herein, "determinant" is used interchangeably with the term "epitope". Such a purified antigen and determinants thereof are useful in the production of monoclonal and polyclonal antibodies for diagnostic and therapeutic applications using techniques well known in the art. For example, purified antigen may be used to immunize animals to generate murine hybridomas expressing monoclonal antibodies specific for the antigen. In other cases, the antigen may be used to stimulate an immune response in a rabbit, goat, non-human primate or other animal from whose serum polyclonal antibodies may be obtained as described, for example, in Ghose et. al., *Methods in Enzyumology*, vol. 93, 326-327 (1983). In addition, the antigen may be used for the purification or characterization of antibodies of interest, e.g., monoclonal antibodies or antibodies present in human tissue or body fluids.

In accordance with the present invention, antibodies having specificity for the antigen characterized herein and methods for their production are also provided. Preferably, such antibodies are monoclonal antibodies possessing immunoreactivity with the tumor-associated antigen of the present invention and are preferably not reactive with carcinoembryonic antigen such as the preferred monoclonal antibody LA20207. Alternatively, antibodies of this aspect of the invention may be polyclonal in origin. Antibodies of the present invention may also include biological or synthetic chimeric and humanized antibodies having specific reactivity with the tumor-associated antigen characterized herein.

The antibodies of the present invention may be useful for the detection, diagnosis and treatment of cancer in humans, particularly lung adenocarcinoma. Such antibodies may be labeled with an imaging marker to permit detection or bound to a suitable therapeutic agent to treat lung cancer. For imaging, antibodies are preferably labeled with a radioisotope such as gamma-emitters, positron-emitters, and x-ray-emitters including, for example, indium-111, technetium-99m, iodine-125, gallium-67, and gallium-68. The antibody, such as LA20207, is preferably labeled with a gamma-emitting label such as indium-111. Suitable therapeutic agents include radioisotopes, drugs, toxins and biological proteins. Radioisotopes include those useful for imaging as well as emitters of alpha and beta particles such as yttrium-90, scandium-47 and iodine-131. Antibodies such as the preferred monoclonal antibody LA20207 are preferably labeled with yttrium-90. Drugs include, in general, alkylating agents, antiproliferative agents, tubulin-binding agents, cytotoxins, and the like, preferably the nitrogen mustard agents, the vinca alkaloids, the daunomycin family, the mitomycins, the bleomycins, the cytotoxic nucleosides, the pteridine family of drugs, and the sulfonylureas described in European Patent Publication No. 222,475, published May 20, 1987. Particularly useful members of the preferred drugs include for example, doxorubicin, daunorubicin, aminopterin, methotrexate, methopterin, dichloromethotrexate, mitomycin C, porfiromycin, 5-fluoroouracil, 6-mercaptopurine, cytosine arabinoside, etoposide, melphalan, vinblastine, vincristine, leurosidine and the like. Toxins suitable as therapeutic agents include the podophyophyllotoxins, ricin, the trichothecenes, the colchicenes and pseudomonas endotoxin. Biological proteins having therapeutic value include hormones, the interferons (alpha, beta and gamma), the interleukins and the like.

Such antibodies may also have application in the isolation and purification of the antigen provided by the invention and the characterization of precise determinants. In this regard, another aspect of the present invention is the substantially pure conformational-dependent protein epitope found on the novel antigen of the present invention and recognized by the antibodies of the present invention. The invention also includes antibodies to this epitope, preferably monoclonal antibodies and more preferably monoclonal antibody LA20207.

Monoclonal antibodies as described above may be produced according to the method of Kohler and Milstein, *Nature* 256, 495–497 (1975) as modified by Gerhard, *Monoclonal Antibodies*, 370–371, R. Kennett et. al. eds. (Plenum Press 1980). In accordance with the present invention, a mouse or other suitable host known to those skilled in the art is immunized with the purified antigen of the invention or a soluble fraction of human tumor tissue derived from a lung adenocarcinoma. Following immunization, the spleen cells of the immunized mouse are fused with suitable mouse myeloma cells to obtain a mixture of hybrid cell lines. Resulting cell lines are cultured in media selective for hybrid cell lines. Surviving hybrids producing monoclonal antibodies, preferably LA20207, having specificity for the antigen characterized herein are thereafter cloned and the monoclonal antibodies produced are recovered.

The present invention additionally includes methods for the in vitro detection of cancer in humans, particularly lung adenocarcinoma. Characterization of the unique tumor-associated antigen of the invention as set forth herein permits its detection in patient tissue specimens. Methods for the in vitro detection of antigens in patient tissue specimens are known to those skilled in the art and include, for example, the immunohistochemical methods taught in Taylor, *Arch. Pathol. Lab. Med.* 102, 113 (1978). Briefly, in the context of the present invention, a sample of tissue specimen obtained from a suspected cancer patient is treated with an antibody, preferably a monoclonal antibody, and more preferably monoclonal antibody LA20207, having specificity for the tumor-associated antigen of the present invention. The sites at which antibody is bound to antigen are thereafter determined by selective staining of the tissue specimen by standard immunohistochemical procedures. Such procedures include, for example, immunoperoxidase staining, avidin-biotin method, and immunofluorescence staining using fluorescein isothiocyanate. A qualitative or quantitative determination of the tumor-associated antigen of the present invention in patient tissue specimens by immunohistochemical or immunoassay procedures is of diagnostic utility and may be indicative of or correlate with the progression of a disease state.

Similarly, methods for the in vitro detection of antigenic substances in biological fluid samples by immunoassay procedures are also well known in the art. Biological fluid samples include serum, plasma, urine, saliva, sweat, ascitic fluid, pleural fluid and other body fluids. For purposes of the present invention, a biological fluid sample may be treated with at least one antibody, preferably a monoclonal antibody, and more preferable monoclonal antibody LA20207, having specificity for the tumor-associated antigen of the present invention. The binding of antibody to antigenic components of the biological fluid sample is thereafter determined by methods disclosed herein or known in the art. For example, qualitative or quantitative determinations of the antigen defined by the invention may be accomplished by competitive or non-competitive immunoassay procedures. Monoclonal antibodies, preferably LA20207, may be used in this aspect of the invention and are preferred. Alternatively, polyclonal antibodies having specificity for the antigen provided by the present invention may also be used. Immunoassays may be used to detect antigenic substances, preferably two-site immunometric assays known to those skilled in the art that employ monoclonal antibodies selected to bind to non-interfering determinants of a target antigen. For example, the two-site immunometric assays described in U.S. Pat. Nos. 4,376,110 and 4,486,530 issued to David et. al. on Mar. 8, 1983 and Dec. 4, 1984, respectively, may be used and are incorporated herein by reference.

The significant localization of an antibody of the present invention to lung adenocarcinoma in human patients demonstrates the usefulness of the invention for in vivo applications. For example, one aspect of the present invention is the in vivo diagnosis and therapy of cancer in humans, particularly lung cancer. Methods for tumor localization and detection may be performed, in accordance with the present invention, by administering to a suspected cancer patient a predetermined effective amount of an antibody having specific reactivity with the tumor-associated antigen of the present invention and detecting the sites of localization of the antibody. The sites of localization may be determined by standard imaging techniques, preferably planar imaging or single photon emission computed tomography (SPECT), and by gamma camera whole-body imaging. The predetermined effective amount of total antibody, labeled and unlabeled, for imaging applications is within the range of about 2 to about 200 mg, preferably in the range of about 5 to about 80 mg, and more preferably about 20 to about 40 mg. The antibody, preferably a monoclonal antibody, and more preferably LA20207, is administered to the patient in a pharmaceutically acceptable carrier and labeled with a marker to permit in vivo detection. For imaging, the antibodies are preferably labeled with the markers described above. Pharmaceutically acceptable carriers useful for imaging and therapy are well-known in the art and include, for example, aqueous solutions such as bicarbonate buffers, phosphate buffers, Ringer's solution and physiological saline supplemented with 5% dextrose or human serum albumin, if desired. A further advantage of the present invention is the discovery that certain antibodies of the present invention may detect sites of lung cancer that are not detected by conventional methods. The course of treatment in such instances may change drastically upon locating tumor sites previously undetected by other methods.

In accordance with methods of the present invention for cancer therapy, a predetermined effective amount of an antibody, preferably a monoclonal antibody, and more preferably monoclonal antibody LA20207, having specificity for the tumor-associated antigen characterized by the invention is administered to a diagnosed cancer patient. The predetermined effective amount of antibody for therapeutic applications is in the range of about 1 to about 100 mg, preferably in the range of about 2 to about 40 mg, and more preferably in the range of about 2.5 to about 10 mg. The monoclonal antibody, preferably LA20207, is administered to the cancer patient in a pharmaceutically acceptable carrier as described above.

A suitable therapeutic agent as described above and selected for delivery to the tumor site may be bound to the monoclonal antibody before administering to a cancer patient or may be separately administered to a patient subsequent to the administration of the monoclonal antibody. Methods for attaching antibodies to such therapeutic agents for cancer therapy are well-known to those skilled in the art. For example, methods of attaching therapeutic agents to antibodies are disclosed in Blair et. al., *J. Immunol. Methods* 59, 129 (1983), Ghose et. al., *Methods in Enzymology* 93, 280 (1983) and in U.S. Pat. No. 4,741,900 to Alvarez et. al. issued May 3, 1988 and incorporated herein by reference. Methods of administering the present therapeutic compositions are also well known and include intravenous, intraperitoneal, intralymphatic, intrathecal and intraarterial infusion or injection.

In still another aspect, pharmaceutical compositions comprising an antibody having specific reactivity with the antigen characterized herein and a pharmaceutically acceptable carrier as described above are provided. Antibodies used in the preparation of the pharmaceutical compositions of the present invention are preferably monoclonal antibodies, and more preferably monoclonal antibody LA20207. The antibodies are optionally labeled or conjugated with imaging markers or suitable therapeutic agents described above.

Additionally, in the context of in vivo cancer diagnosis and therapy, those skilled in the art will appreciate that antibody preparations comprising mixtures of antibodies or fragments thereof having specificity for the tumor-associated antigen of the present invention may be used in certain instances to enhance the detection, localization and treatment of tumors.

EXAMPLE 1

Production of Monoclonal Antibody LA20207

Tumor cytosol obtained from human lung adenocarcinoma was used as the immunogen to produce hybrid cell line ATCC Deposit #HB 10224 generating monoclonal antibody LA20207. A human lung adenocarcinoma specimen (A00239-01, Veterans Hospital Cancer Center, La Jolla, Calif.) was collected in an autopsy within ten hours after death and stored at $-80°$ C. To prepare crude cytosol and membrane, the specimen was first homogenized in 4 volumes of 10 mM tris-HCl, pH 7.5, 2mM calcium chloride, and 2mM phenylmethylsulfonate (homogenization buffer) at $4°$ C. in a Dounce homogenizer. All subsequent steps were carried out at $4°$ C. The homogenate was centrifuged at $1000 \times g$ for 5 minutes to remove nuclei and intact cells. The supernatant was removed and the pellet centrifuged at $100,000 \times g$ for one hour. After the high speed centrifugation, the supernatant containing the cytosol fraction was removed and stored at $-80°$ C. The pellet, containing the crude membrane portion, was resuspended in one volume of homogenization buffer, aliquoted and stored at $-80°$ C.

Female Balb/c mice (Charles River Breeding Laboratories, Wilmington, MA) were each immunized with 100 µg of A00239-01 lung adenocarcinoma cytosol on alumina c-gamma (Sigma, St. Louis, MO) interperitoneally. The mice were again immunized twenty days later with 100 µg cytosol on alumina c-gamma interperitoneally and given a final boost with 100 µg cytosol on alumina c-gamma eighty-one (81) days after the second immunization.

Three days after the final immunization, spleens were aseptically removed from the mice into AP-MEM media (Flow Laboratories, Inglewood, California). After the spleens were carefully disrupted to release splenoctyes into the media, the clumps of cells were disassociated by pipetting and transferred to a centrifuge tube. Upon standing for about 5 minutes, the cell suspension was removed from the sedimented materials and centrifuged at $1,000 \times g$ for 5 minutes. After washing and a second centrifugation at $1,000 \times g$ for 5 minutes, the resulting splenoctye pellet was resuspended in AP-MEM media.

Cell fusion was carried out according to the procedure of Kohler and Milstein, *Nature* 256, 495-497 (1975) as modified by Gerhard, *Monoclonal Antibodies*, R. Kennett et. al., 370-371 (plenum press 1980). Briefly, $1 \times 10^8$ splenocytes were fused with $2.5 \times 10^7$ P3-X63-Ag8.653 (ATCC #CRL 1580), a mouse myeloma cell line, in 1.0 ml of 35% polyethylene glycol (PEG 1500) in AP-MEM medium. Following the fusion, cells were cultured in medium supplemented with a HAT (hypoxanthine, aminopterin, thymidine) solution (1 ml HAT/100 ml media) at $37°$ C. in a humidified 5% $CO_2$ incubator. To prepare the HAT solution, 2 ml of 5M NaOH and 8 ml of deionized water were added to 408 mg of hypoxanthine, 116.1 mg of thymidine and 6.7 mg of glycine and swirled until completely dissolved. Following the addition of 140 ml of deionized water, the solution was sterilized with a 0.2 micron 500 ml Nalgo filter unit.

Antibodies produced by the resulting hybridomas were screened by an enzyme-linked immunoabsorbent binding assay (ELISA) on cytosol preparations of A00239-01, the immunizing lung adenocarcinoma tissue specimen, and crude membranes prepared from human liver tissues. Briefly, 1 µg/well of A00239-01 cytosol or liver membranes were first aliquoted onto the wells of a 96-well microtiter plates and dried overnight. The wells were then washed 3 times with 0.3% gelatin, 1% bovine serum albumen (BSA) in phosphate buffered saline (PBS: 0.01 M sodium phosphate plus 0.41 M NaCl). Fifty µl of culture supernatants containing up to about 100 µg/ml were removed and applied to each well, followed by a 1 hour incubation at room temperature. After 5 washes with 0.3% gelatin/PBS, 50 µl of goat anti-mouse IgG-Biotin (Zymed) diluted 1:1000 in PBS plus 10% horse serum was added as the secondary antibody and incubated for 1 hour. After 6 washes, 50 µl of a mixture comprising reagents A (avidin) and B (biotin-horseradish peroxidase) was added to each well and incubated for 30 minutes at room temperature. The mixture was prepared by diluting reagent A and reagent B (1:1000) in PBS supplemented with 10% horse serum. Reagents A and B may be obtained from Vector. The excess avidinbiotin complex was removed by washing each well six (6) times. Then 200 µl of 1 mg/ml α-phenylenediamine (OPD), 0.03% $H_2O_2$ in 0.1 M citrate phosphate buffer (hereinafter referred to as OPD developing solution) was added to develop color. The plate was incubated in the dark for 30 minutes, followed by the addition of 50 µl/well 4N $H_2SO_4$ to stop the reaction. The optical density (O.D.) was read at 490 nm.

Antibodies demonstrating a 5-fold or greater reactivity with the tumor cytosol compared with normal liver membranes were selected. As a result of the selection method, monoclonal antibody LA20207 was further characterized and selected for use in the antigen characterization as provided herein. Based on these results, LA20207 was used for in vivo studies to determine the effectiveness of using the antibodies of the present invention for the detection and treatment of human lung cancer.

EXAMPLE 2

Characterization of Monoclonal Antibody LA20207

A. Radioimmunoassay

Monoclonal antibody LA20207 was screened against a panel of human tumors to determine the presence of antigen reactive with the antibody. The tumors screened with LA20207 are listed in Table 1.

Cytosol lysate from the tumors were prepared by first mincing about 1 gm of solid tumor through a tissue press into a petri dish. The minced tumor was then suspended in 3 ml of 10mM tris-HCl, 2mM calcium chloride, and 2mM phenylmethylsulfonate homogenization buffer and transferred to a cold Dounce homogenizer. After adding approximately 3 ml of 0.5% NP-40 detergent, the suspended lysate was dounced gently until a homogenous solution was obtained. The homogenized solution was thereafter centrifuged at 1000 ×g in a Sorvall GLC-2B desk top centrifuge for 15 minutes. The supernatant containing the crude cytosol lysate was stored at −70° C. and thawed before use. The protein concentration of the thawed crude lysate was determined by a Bio-Rad Protein Assay following the manufacturer's instructions and adjusted to 2.5 mg/ml with phosphate buffered solution (PBS). Glass fiber disks positioned in the wells of a Cleveland plate were pre-washed with PBS and vacuumed prior to the addition of 5 µg/well of the crude lysate and incubation for 15 minutes. After vacuuming off the unbound lysate, 50 µl/well of a blocking agent (3% albumin or 8% fetal calf serum) was added and allowed to stand for 5 minutes, followed by 2 washes with PBS. The disks were then incubated at room temperature for 1 hour with antibodies labelled with $^{125}$iodine at $10^5$ cpm/disk. After the 1 hour incubation, the disks were washed and vacuumed 3 times with PBS and total counts were determined on a conventional gamma counter.

The reactivity of monoclonal antibodies LA20207 and KS1/4 are shown in Table 1. The results are reported as subjective values (neg, +/neg, +, 1+, 2+, 3+, 4+) based on relative binding.

TABLE 1

| Name | Tumor Type | Source | LA20207 | KS1/4 |
|---|---|---|---|---|
| LS174T | colon ca | ATCC CL188 | Neg | 2+ |
| SW403 | colon ca | ATCC CCL230 | Neg | |
| SW620 | colon ca | ATCC CCL227 | Neg | |
| T183 | colon ca | UCSD | Neg | |
| T380 | colon ca | UCSD | Neg | 1+ |
| A00239 | lung adeno | VA | 2+ | |
| A549 | lung adeno | ATCC CCL185 | Neg | + |
| Calu3 | lung adeno | ATCC HTB-55 | Neg | 2+ |
| CH27LCI | lung adeno | U. of WA (Hellstrom) | Neg | Neg |
| P3/UCLA | lung adeno | Eli Lilly & Co | Neg | 2+ |
| T392 | epidermoid/adeno | UCSD (Kaplan) | + | |
| M103 | small cell lung | VA (Deftos) | Neg | |
| NCIN417 | small cell lung | NCI (Mulshine) | Neg | |
| T293 | small cell lung | UCSD | Neg | |
| Clouser | breast ca | NCI (Schlom) | Neg | |
| H925 | breast ca | U. of WA (Hellstrom) | Neg | Neg |
| MCF7 | breast ca | ATCC HTB 22 | Neg | |
| MX1 | breast ca | B.L. Memorial Oakland | Neg | |
| SKBR3 | breast ca | ATCC HTB 30 | Neg | |
| T386 | breast ca | UCSD | Neg | |
| T417 | breast ca | UCSD | Neg | |
| 4-2169T2 | melanoma | U. of WA (Hellstrom) | Neg | Neg |
| Brown | melanoma | St. Joseph Hosp. | Neg | |
| COLO38 | colon ca | Columbia (Ng) | Neg | |
| CRML4 | melanoma | Charles River (Shek) | Neg | |
| M21 | melanoma | Columbia (Ng) | Neg | Neg |
| SKMEL28 | melanoma | ATCC#HTB-72 | Neg | |
| DU145 | prostate ca | UCSD/VA (Sobel/Glassey) | + | |
| P3 | prostate ca | UCSD (Glassey) | Neg | 3+ |

ATCC = American Type Culture Collection
NCI = National Cancer Institute
UCSD = University of California at San Diego
VA = Veterans Administration Hospital, La Jolla, CA
ca = carcinoma

B. Immunohistochemical Determination of LA20207

The presence of antigen reactive with LA20207 in normal and tumor tissue was determined by immunoperoxidase staining of human tissue.

An indirect immunoperoxidase assay, essentially as described by Taylor, *Arch. Pathol. Lab. Med.* 102, 113 (1978), was used to stain the sections. Frozen tissue blocks, obtained from surgical and autopsy specimens collected within ten hours after death and stored at −80° C., were sliced into 4-6 micron sections on a microtome/cryostat and mounted on glass slides coated with an adhering agent. Any adhering agent known to those skilled in the art may be used. The sections were briefly air-dried and rehydrated by incubating in PBS for 5 minutes. The sections were then pre-treated with 10% normal goat serum in PBS for 15 minutes. Following overlay with supernatant containing LA20207 antibody at 1 µg/ml, the sections were incubated in a humid chamber for 1 hour. The sections were then washed with PBS to remove unbound antibody and immersed in PBS for 5 minutes. After overlaying the sections with a 1:50 dilution of peroxidase-conjugated goat anti-mouse IgG and IgM antibody (Tago Chemicals, Burlingame, CA), they were incubated for 30 minutes in a humid chamber, followed by washings with PBS to remove unbound secondary antibody. Color was developed by the addition of 1 mg/ml of diaminobenzidine in 0.03% $H_2O_2$ and thereafter counterstained with hematoxylin eosin.

The results, summarized in Table 1 below, demonstrate the reactivity of monoclonal antibody LA20207 with normal kidney and lung tissues, as measured by the intensity of staining of such tissue. The mean intensity of staining is reported on a scale of 0 to 4+ based on relative binding. By comparison, LA20207 demonstrated no reactivity with other normal tissues tested.

TABLE 2

| Immunohistological Reactivity of LA20207 on Normal Tissue | |
|---|---|
| Tissue | No. Positive/Total Examined |
| Adrenal | 0/2 |
| Bladder | 0/2 |
| Brain | 0/2 |
| Breast | 0/8 |
| Cervix | 0/2 |
| Colon | 0/8 |
| Diaphragm | 0/1 |
| Duodenum | 0/1 |
| Esophagus | 0/2 |
| Heart | 0/2 |

TABLE 2-continued
Immunohistological Reactivity of LA20207 on Normal Tissue

| Tissue | No. Positive/Total Examined |
|---|---|
| Ileum | 0/1 |
| Jejunum | 0/1 |
| Kidney | 2/2 (3+) |
| Liver | 0/2 |
| Lung | 8/9 (3+) |
| Ovary | 0/2 |
| Pancreas | 0/2 |
| Peripheral Nerve | 0/8 |
| Placenta | 0/2 |
| Prostate | 0/8 |
| Salivary gland | 0/1 |
| Skin | 0/1 |
| Spleen | 0/2 |
| Spinal Cord | 0/1 |
| Testes | 0/2 |
| Thymus | 0/1 |
| Thyroid | 0/2 |
| Tonsil | 0/2 |
| Ureter | 0/1 |
| Urethra | 0/1 |
| Vagina | 0/1 |

As shown in Table 3 below, monoclonal antibody LA20207 is strongly reactive with lung adenocarcinoma and not reactive with the other carcinomas tested.

TABLE 3
Immunohistological Reactivity of LA20207 on Tumor Tissue

| Tissue | No. Positive/Total Examined |
|---|---|
| Lung adenocarcinoma | 8/9 (3+) |
| Breast Ca | 0/8 |
| Colon Ca | 0/11 |
| Gastric Ca | 0/4 |
| Lung Broncheo-Alvealor Ca | 0/2 |
| Lung Epidermoid Ca | 0/2 |
| Lung Large Cell Ca | 0/2 |
| Lymphoma | 0/2 |
| Melanoma | 0/4 |
| Pancreatic Ca | 0/2 |
| Prostate Ca | 0/8 |
| Rectal Ca | 0/2 |
| Renal Ca | 0/4 |
| Sarcoma | 0/2 |
| Testicular Ca | 0/4 |
| Thyroid Ca | 0/2 |

Normal primate lung and kidney tissues were compared with human tissues for reactivity with LA2-2-7. The tests demonstrated no correlation as shown in Table 4 below. Results are reported as the mean intensity of staining on a scale of 0–4+.

TABLE 4
Comparison of Human and Primate Normal Tissue Reactivity

| Origin | Kidney | Lung |
|---|---|---|
| Human | 3+ (t) | 3+ (Bas) |
| Primate: | | |
| Cynotnolgous | 0 | 2+ (a) |
| African Green | 3+ (g) | 1+ (a) |
| Rhesus | 1+ (g) | 0 |
| Baboon | 2+ (g) | 0 |
| Chimpanze | 0 | 0 |

Abbreviations:
t = tubular epithelium
b = bronchus
a = alveolar epithelium
g = glomeruli
s = Stroma

C. Isotope Determination of LA20207

Goat anti-mouse IgG, $IgG_{2A}$, $IgG_{2B}$, $IgG_3$ and IgM (Tago, Burlingame, Calif.) were first diluted 1:3000 in a 10mM sodium phosphate buffer solution (pH 7.2) from stock concentrations of 1 mg/ml protein. The test wells of a 96-well polyvinyl microtiter plate were first coated with the diluted goat anti-mouse Ig at 50 μl per well and incubated overnight at 37° C. The plate was then washed with PBS-0.1% Tween followed by a second wash with distilled water. To each test well, 200 μl of a blocking solution was added to each well and the covered plate stored at 4° C. The blocking solution was prepared by slowly adding 20 gm BSA (Sigma), 2 ml Tween-20 (Sigma) and 20 ml 10% sodium azide to 2 liters of PBS with constant stirring.

Within five days, the plate was washed with PBS-0.1% Tween followed by a second wash with distilled water at room temperature. Next, 40 μl of LA20207 antibody supernatant at a concentration of 10μg/ml, positive IgG and IgM controls and HAT media (used as a negative control) were added to the test wells, covered, and incubated at 37° C. for one hour. After washing the plate three times with PBS-0.1% Tween and once with distilled water, 100 μl of freshly made OPD developing solution was added to each well. The plate was immediately covered with foil and incubated at room temperature for 15 minutes with shaking. To stop the reaction, 50 μl of 4N $H_2S_2$ was added to each well and the plate was read at 490 nm on an ELISA reader.

Following the procedure described above, the isotype of monoclonal antibody LA20207 was determined to be of the murine $IgG_1$ class.

D. Flow Cytometry

To determine whether the antigen of the present invention is associated with blood components, the reactivity of LA20207 with blood components, including lymphocytes, red blood cells, myeloid components, and platelets was evaluated. Methods of performing flow cytometry are known to those skilled in the art and are described, for example, in H. M. Shapiro, *Practical Flow Cytometry* (Alan R. Liss 1988).

Freshly drawn heparinized blood was centrifuged twice at 1000 ×g for 5–8 minutes each. From this, plasma was collected and centrifuged at 1000 ×g for four to six minutes to pellet the platelets which were resuspended in an appropriate volume of plasma. The buffy layer was also collected and centrifuged twice at 1000 ×g for four to six minutes each to collect lymphocytes. About 10–12 ml of a 0.83% ammonium chloride-0.14% potassium bicarbonate-0.05mM EDTA solution, pH 7.3, was added to the buffy pellet, incubated for 5 minutes and centrifuged again at 1000 ×g for four to six minutes. The pellet was washed once and resuspended in RPMI-10% fetal bovine serum at a concentration of 40 ×$10^6$ cells/ml. Red blood cells were also resuspended in RPMI-10% fetal bovine serum at a concentration of 40 ×$10^6$ cells/ml.

50 μl of LA20207 supernatant was dispensed into 96-well microtiter plates, followed by 25 μl ($10^6$ cells) of cell suspension and incubated for 30 minutes at 4° C. Cells were washed three times with PBS by centrifugation and incubated with 50 μl of goat anti-human IgM-FITC conjugate (Tago Burlingame, CA) for 30 minutes at 4° C. Cells were again washed as before, transferred to tubes containing 0.5–1.0 ml formalin and subjected to analysis on a fluorescence activated cell sorter. The above analysis indicated no specific reactivity of LA20207 with any blood components as shown in Table 5. Therefore, the antigen of the present invention is not associated with blood components. The data is reported as percent positive to mean intensity of fluorescence (MIF).

TABLE 5
Flow Cytometry Data

| | % Pos:MIF |
|---|---|
| Blood: | |
| Erythrocytes | <1:<10 |
| Lymphocytes | 4:32 |
| Monocytes | 1:50 |
| Granulocytes | 3:36 |
| Platelets | 11:27 |
| Marrow: | |
| Lymphoid/Erythroid | <1:<10 |
| Myeloid | <1:<10 |

EXAMPLE 5

Purification of Monoclonal Antibody LA20207

Monoclonal antibody LA20207 was purified from 278 ml of pooled ascites fluid obtained from pristane-primed Balb/c mice injected interperitoneally with 1 × 10$^7$ LA20207 hybridoma cells (ATCC #HB 10224). Ascites preparation and harvesting methods are described in Galfre and Milstein, *Methods in Enzymology*, Vol. 73B, 43–45, Langone & Van Vunakis, eds. (Academic Press 1981).

The pooled ascites fluid was centrifuged at 4° C. for 20 minutes at 11,000–18,000 ×g. The antibodies were precipitated from the supernatant fraction by adding about ml of a 25% sodium sulfate solution with continuous slow stirring at room temperature. The resulting mixture was allowed to stand for 1.5 hours at room temperature and thereafter centrifuged at room temperature for about 20 minutes at 11,000–18,000 ×g. Following the removal of the supernatant fraction, 180 ml of 18% sodium sulfate was then added to the precipitated material to form a homogenous solution and centrifuged at room temperature for 20 minutes at 11,000–18,000 ×g. The precipitate was dissolved in 84 ml of 50mM sodium phosphate (pH 8.2) and dialyzed at 4° C. against 2 liters of 50mM sodium phosphate buffer solution (pH 8.2) for 43 hours with one change of buffer after 16 hours. The dialyzed antibody solution was then diluted with 389 ml sterile water and centrifuged at 15,000 ×g for 20 minutes at 4° C. The supernatant fraction containing LA20207 antibody was carefully removed and filtered for further purification. After filtering, the antibody was further purified by using a 190 ml DEAE Sephacel (Pharmacia) column equilibrated with 0.01M sodium phosphate (pH 8.2, conductivity 1.8 mMHO). After loading the antibody solution onto the DEAE column with 0.01M sodium phosphate (pH 8.2, conductivity 1.8 mMHO), the column was first washed with 0.025M sodium phosphate buffer solution (pH 8.2, conductivity 3.6 mMHO), and then eluted with 0.05M sodium phosphate (pH 8.2, conductivity 6.4 mMHO). Fractions having an absorbance greater than 1.0 at 280 nm on an UV monitor were collected, pooled and stored at 4° C.

EXAMPLE 6

Preparation of $^{111}$-In-Labeled LA20207

Radiolabelling LA20207 with Indium-111 was accomplished through the chelating agent diethylenetriamine-pentaacetic acid (DTPA). First, 3.0 ml of 10mM DTPA (pH 9.5) was added to 23.3 ml of 6.45 mg/ml purified LA20207 antibody. The pH of the antibody-DTPA solution was adjusted to about 9.5 using 0.3 ml 1M Na$_2$CO$_3$ (pH 12) solution. Next, the antibody concentration was adjusted to 5 mg/ml by adding 3.4 ml of 95mM NaHCO$_3$ with gentle stirring for 15 minutes at room temperature. While the antibody solution was stirring, a $^{111}$In(III) isothiocyanate solution (ITC solution) was prepared by adding 0.49 ml of 0.6mM sodium phosphate (pH 8 2) to 0.49 ml of 37mM $^{111}$IN(III) isothiocyanate. Immediately after preparing the ITC solution, 1.16 ml of the solution was added to the antibody-DTPA solution followed by continuous stirring at room temperature for 2.5 hours. The reaction was thereafter quenched by cooling to 0° C.

After loading the labeled antibody conjugate mixture onto a P-6DG Sephadex column (Pharmacia), the column was eluted with 0.13mM ammonium citrate (pH 6.0) at a 70 ml/hr flow rate. Using a UV monitor, all fractions of the eluant having an absorbance (A$_{280}$) of greater than 0.1 were collected and tested for indium-111 incorporation. Fractions having the highest incorporation were pooled, resulting in a pool volume of 34.6 ml containing about 132 mg antibody to which 0.6 ml of 25% normal serum albumin was added. The resulting antibody solution was adjusted to a final concentration of 1 mg/ml with 96.6 ml of 0.13mM ammonium citrate (pH 6.0), sterile filtered and stored at 4° C.

Tests to compare the reactivity of unconjugated and conjugated LA20207 antibody were performed to determine the effect of conjugation on the reactivity of the antibody. Purified and conjugated LA20207 antibody were tested in ELISA against 1 μg/well cytosol extracted from the A00239-01 lung adenocarcinoma tissue specimen prepared according the method described in Example 2. The results indicate that the conjugated form of LA20207 (59% immunoreactivity) exhibits no significant loss of reactivity compared with the unconjugated form (65% immunoreactivity). In addition, conjugation by this method produced the desired 2 chelates/antibody and indium incorporation of more than 90%.

EXAMPLE 7

Antigen Characterization: Molecular Weight Determination

The molecular weight of the novel antigen of the present invention was determined by HPLC using two gel filtration columns, a 9.4 ×250 mm GF-250 Zorbak column (Dupont) connected to a 9.4 ×250 mm GF-450 Zorbak column (Dupont). A 12.5×4mm GF-250 Zorbak guard column (Dupont) preceded both filtration columns. Techniques to determine the molecular weight by HPLC analysis are well-known to those skilled in the art such as those described, for example, in E. Johnson & R. Stevenson, Basic Liquid Chromatography, 149–164 (Varion Assoc. 1978). Briefly, from 1–5 mg of lung adenocarcinoma A00239-01 cytosol in 50 μl of a 0.2M sodium phosphate, 0.3M sodium chloride solution (pH 7.0) was injected into the HPLC system. Fractions of 300 μl each were collected at a flow rate of 1.0 ml/minute and assayed by ELISA. An aliquot of each fraction was pipetted onto a microtiter plate at 50 μl/well and allowed to dry overnight at 37° C. On the following day, the dried fractions were assayed for reactivity with LA20207 following the general procedure described in Example 1.

To determine the molecular weight of the novel antigen of the present invention, a standard curve was produced with the use of gel filtration standards (Biorad) fractionated through the HPLC columns and monitored at O.D. 280. Using the standard curve, the native molecular weight of the antigen recognized by LA20207 was determined to be in the range of about 50–80 Kd, preferably about 67 Kd. A smaller component reactive with LA20207 was also observed in the molecular weight range of about 20–30 Kd, preferably about 28 Kd. This component is believed to be a breakdown product of the native antigen. FIG. 1 shows the reactivity of LA20207 with the collected fractions of the antigen obtained by HPLC.

EXAMPLE 8

Antigen Characterization Isoelectric Focusing

Isoelectric point of the antigen characterized by LA20207 was determined using an isoelectric focusing column. Five mg of A00239-01 lung adenocarcinoma cytosol prepared as described in Example 1 was focused in a water-jacketed 110 ml isoelectric focusing column in a 0–47% sucrose gradient containing ampholytes of the pH range 3.5–10. The column was pre-focused at 600 volts for 12 hours at 4° C. prior to injecting each sample into the middle of the gradient followed by focusing for an additional 30 hours at 4° C. One ml fractions were collected from the column and the pH was immediately measured. Collected fractions were dialyzed overnight against 10mM sodium phosphate pH 7.0. Aliquots were examined for reactivity with the LA20207 antibody in an ELISA assay against cytosol preparations of the A00239-01 lung adenocarcinoma specimen.

Isoelectric focusing of the antigen by this technique revealed an isoelectric point in the range of about 4.9 to about 6.5, with a peak at about 5.6.

EXAMPLE 9

Antigen characterization: Epitope Analysis

To determine the nature of the epitope recognized by monoclonal antibody LA20207, 20 μg of A00239-01 human tumor cytosol prepared as described in Example 1 was subjected to the following destructive treatments and tested for reactivity with LA20207 by ELISA:

(a) Methanol: incubated in 95% methanol for 1 hour at 4° C.

(b) Neuraminidase: incubated for 1 hour at 37° C. with 100 units/ml of *C. perfringens* neuraminidase (Sigma, St. Louis).

(c) Periodate: incubated in 1mM sodium periodate for 30 minutes at room temperature, and reduced with 10mM sodium borohydride.

(d) Heat: cytosol was subjected to 100° C. for 20 minutes.

(e) Reduction/Alkylation: incubated in 6M guanidine-HCl, 10mM DTT for 4 hours at 45° C., followed by incubation in 10mM iodoacetic acid for 30 minutes at 23° C.

(f) Urea: incubated in 8M urea for 18 hours at 45° C.

The results of the destructive treatments are set forth in Table 6 below. The lung adenocarcinoma A00239 cytosol was plated out at 1 μg/well and dried overnight at 37° C. Treatments designed to identify carbohydrate epitopes, such as periodate and neuraminidase, had no significant effect. The treatments used to identify protein epitopes (heat, urea and guanidine-HCl) significantly reduced the reactivity of LA20207 with the treated antigen. Although the effect of the methanol treatment, used to identify lipid epitopes, is inconclusive, methanol treatment is known to denature proteins as well. Therefore, the combination of the protein destructive treatment results and the inconclusive methanol result suggest that LA20207 recognizes a conformationaldependent protein opitope.

TABLE 6

Monoclonal Antibody LA20207
Destructive Treatment of A00239-01 Cytosol

| Treatment | % activity Remaining (average) | Range of Controls | Conclusions |
| --- | --- | --- | --- |
| Control | 100 | | |
| Methanol | 36 | (+) 0–6% | inconclusive |
| | | (−) 69–100% | |
| Neuraminidase | >100 | (+) 0–4% | non-carbohydrate |
| | | (−) 88–100% | epitope |
| Periodate | 90 | (+) ≦10% | non-carbohydrate |
| | | (−) >75% | epitope |
| Heat | 1.7 | (+) 0–6% | conformational |
| | | (−) ≧50% | protein epitope |
| 6M Guanidine-HCl | <1 | (+) ≦15% | conformational |
| | | (−) ≧75% | protein epitope |
| 8M Urea | <1 | (+) ≦20% | conformational |
| | | (−) ≧75% | protein epitope |

EXAMPLE 10

In Vivo Investigations

A. Biodistribution

In a 48-hour diodistribution study, six (6) normal Swiss Webster mice (Simonsen Laboratories) were each injected with 46 μCi of $^{111}$-In-labeled LA20207 at a dose of 5 μg in 100 μl. Organs and excretions were extracted or collected, weighed, if appropriate, and measured for radioactivity by conventional method swell known to those skilled in the art. The results of the biodistribution study, provided in Table 7 below, indicate that the dosimetry calculations for liver and blood at 48 hours were excellent and the radiation uptake for the other organs was normal.

TABLE 7

In Vivo Biodistribution of LA20207 at 48 Hours

| Tissue | % Dose/Gram | % Dose/Organ |
| --- | --- | --- |
| Blood | 15.2 | 26.8 |
| | ±4.9 | ±2.8 |
| Bone (Femur) | 2.7 | 6.8 |
| | ±0.8 | ±1.5 |
| Heart | 4.7 | 0.6 |
| | ±2.5 | ±0.3 |
| Kidney | 5.3 | 1.0 |
| | ±6.1 | ±0.2 |
| Liver | 6.1 | 8.3 |
| | ±1.6 | ±1.8 |
| Lung | 8.5 | 1.7 |
| | ±3.0 | ±0.7 |
| Muscle | 1.1 | 11.6 |
| | ±0.2 | ±1.4 |
| Skin | 3.3 | 12.3 |
| | ±0.7 | ±1.7 |
| Spleen | 5.2 | 0.5 |
| | ±2.6 | ±0.1 |
| Intestine | 1.0 | 4.1 |
| | ±0.2 | ±0.4 |
| Urine | | 4.4 |
| Feces | | 5.5 |

B. Clinical Investigations

In a clinical biodistribution study, eight patients were injected intravenously with LA20207. Four of the patients each received 2 mg of ::: indium-labeled antibody (5 mCi) and 3 mg of unlabeled "cold" antibody, while the remaining four patients each received 2 mg of labeled LA20207 (5 mCi) and 18 mg cold antibody. All patients were imaged on days 0, 1, 3 and 6 by the gamma camera whole body imaging technique described in P. H. Brown et. al. "A Simplified Method for Measurement of Biodistribution and Dosimetry of $^{111}$In Monoclonal Antibody by While Body Imaging," *Clin. Nucl. Med.* 12:95, p.11+(1987) to determine the biodistribution and clearance of the injected antibody. Urine and blood samples were collected periodically up to 72 hours. The percent of injected activity, residence time and absorbed dose for selected organs are reported in Table 8. The percent of injected radioactivity in the urinary bladder was calculated using the urine data as described in P. H. Brown et. al., "Radiation Dose Calculation for Tc-99m HIDA in Health and Disease," *J. Nucl. Med.* 22:177–83 (1981). Urine and blood data are provided in Table 9.

TABLE 8

Biodistribution of $^{111}$In-LA20207 in Human Patients

| Organ | Days After Injection (% Dose) | | | | Residence Time (hrs) | Absorbed Dose |
|---|---|---|---|---|---|---|
| | 0 | 1 | 3 | 6 | | |
| Whole Body | 100 | 92.8 | 86.1 | 79.1 | 67.7 | 0.49 |
| Heart | 7.16 | 5.89 | 4.54 | 2.90 | 4.56 | 1.47 |
| Liver | 7.45 | 8.57 | 9.30 | 9.15 | 8.79 | 1.41 |
| Lungs | 9.77 | 7.46 | 6.33 | 4.18 | 6.00 | 1.23 |
| Brain | 1.32 | 1.35 | 1.25 | 1.06 | 1.21 | 0.32 |
| Kidneys | 1.33 | 1.67 | 1.74 | 1.39 | 1.55 | 1.21 |
| Spleen | 1.06 | 1.22 | 1.31 | 0.95 | 1.12 | 1.37 |
| Urinary Bladder | — | — | — | — | 0.21 | 0.47 |

TABLE 9

$^{111}$In-Labeled LA20207 Injected Dose Percent In Urine and Blood

| Urine: | Time Post Injection (Hours) | | | | | | |
|---|---|---|---|---|---|---|---|
| | 0–2 | 2–4 | 4–8 | 8–24 | 24–48 | 48–72 | 0–72 |
| Total % Dose | 1.87 | 0.76 | 1.76 | 2.15 | 1.91 | 2.36 | 10.8 |

| Blood: | | | | | | | | | | | |
|---|---|---|---|---|---|---|---|---|---|---|---|
| | 1 | 1.2 | 1.5 | 2 | 2.5 | 3 | 4 | 5 | 24 | 48 | 72 | 144 |
| % Dose | 86.4 | 88.1 | 86.5 | 85.5 | 84.3 | 84.1 | 82.0 | 79.7 | 59.6 | 47.0 | 36.7 | 20.7 |

To test the potential effectiveness of the antibodies of the present invention for the in vivo detection and therapy of lung cancer, monoclonal antibody LA20207 was administered to thirteen patients with known lung cancer. One (1) mg of LA20207 labeled with 4–5 mCi 111-indium and 4, 19 or 20 mg of unlabeled LA20207 were infused intravenously such that the patients received a total antibody amount of 5, 20 or 21 mg. Planar images were taken on the third day after infusion, with planar or SPECT images taken on days 6 or 9 after infusion. The primary lung cancer was surgically removed on day 7 or 10 and measured for antibody concentration. Detection of know lesions was determined to be 70% for LA20207. The results of the study reported in Table 10 demonstrate the usefulness of monoclonal antibody LA20207 for in vivo applications.

TABLE 10

| Total Ab Dose | No. of Cases | Known Sites | Known Sites Imaged | % of Known Sites | Previously Unknown Sites deleted |
|---|---|---|---|---|---|
| 5.0 | 8 | 17 | 12 | 71 | 5 |
| 20.0 | 3 | 3 | 2 | 67 | 0 |
| 21.0 | 2 | 3 | 2 | 67 | 1 |
| Totals | 13 | 23 | 16 | 70% | 6 |

The foregoing description of the invention is exemplary for purposes of illustration and explanation. It will be apparent to those skilled in the art that changes and modifications will be possible without departing from the spirit and scope of the invention. It is intended that the following claims be interpreted to embrace all such changes and modifications.

What is claimed is:

1. An isolated tumor-associated antigen, said antigen comprising the characteristics of (1) reactivity with monoclonal antibody LA 20207 generated by ATCC No. HB 10224, (2) a molecular weight within a range of about 50 Kd to about 80 Kd as determined by HPCL gel filtration, and (3) an isoelectric point in solution within a range of about 4.9 to about 6.5.

2. The antigen of claim 1, wherein said isoelectric point is about 5.6.

3. The antigen of claim 1, wherein said antigen is expressed by human lung adenocarcinoma.

* * * * *